United States Patent
Särkelä et al.

(10) Patent No.: US 7,783,343 B2
(45) Date of Patent: Aug. 24, 2010

(54) MONITORING OF THE CEREBRAL STATE OF A SUBJECT

(75) Inventors: Mika Särkelä, Helsinki (FI); Hanna E. Viertiö-Oja, Espoo (FI); Satu Jääskeläinen, Piispanristi (FI); Jaakko Långsjö, Seinäjoki (FI); Anu Maksimow, Turku (FI); Elina Salmi, Turku (FI); Harry Scheinin, Piispanristi (FI)

(73) Assignee: The General Electric Company, Helsinki (FI)

( * ) Notice: Subject to any disclaimer, the term of this patent is extended or adjusted under 35 U.S.C. 154(b) by 1229 days.

(21) Appl. No.: 11/176,944

(22) Filed: Jul. 7, 2005

(65) Prior Publication Data

US 2007/0010755 A1    Jan. 11, 2007

(51) Int. Cl.
*A61B 5/04* (2006.01)
(52) U.S. Cl. .................. 600/545; 600/544; 600/546
(58) Field of Classification Search ................. 600/545, 600/546, 345, 347, 365
See application file for complete search history.

(56) References Cited

U.S. PATENT DOCUMENTS

| 5,320,109 A * | 6/1994 | Chamoun et al. | ........... 600/544 |
| 2003/0055355 A1 * | 3/2003 | Viertio-Oja | ................. 600/544 |

OTHER PUBLICATIONS

*A comparison of bispectral index and ARX-derived auditory evoked potential index in measuring the clinical interaction between ketamine and propofol anaesthesia*, H. E. M. Vereecke et al., Anaesthesia, 2003, 58, pp. 957-961.

*The effect of ketamine on clinical endpoints of hypnosis and EEG variables during propofol infusion*, T. Sakai et al., Acta Anaesthesiol Scand 1999; 43: 212-216.

*Comparative effects of ketamine on Bispectral Index and spectral entropy of the electroencephalogram under sevoflurane anaesthesia*, P. Hans et al., British Journal of Anaesthesia 94 (3): 336-40 (2005).

*Bispectral analysis of the electroencephalogram does not predict responsiveness to verbal command in patients emerging from xenon anaesthesia*, T. Goto, British Journal of Anaesthesia 85 (3): 359-63 (2000).

*Automatic Analysis and Monitoring of Burst Suppression in Anesthesia*, Mika Sarkela et al., Journal of Clinical Monitoring and Computing 17: 125-134, 2002.

*A Primer for EEG Signal Processing in Anesthesia*, Ira J. Rampil, Anesthesiology 1998; 89-980-1002.

Petropulu, Athina P., "Higher-Order Spectral Analysis", The Biomedical Engineering Handbook, Second Edition, vol. 1, CRC Press in cooperation with IEEE Press, 2000, pp. 57-1-57-17.

* cited by examiner

*Primary Examiner*—Patricia C Mallari
(74) *Attorney, Agent, or Firm*—Andrus, Sceales, Starke & Sawall, LLP (57) ABSTRACT

The invention relates to a method and apparatus for monitoring the cerebral state of a subject. At least one of a first and second parameters is derived from the physiological signal data obtained from the subject, wherein the first parameter is indicative of the sum of spectral values of the physiological signal data in a first frequency band lying above high frequency EEG activity and the second parameter is indicative of the relative magnitudes of a first sum of k-th order spectral values and a second sum of n-th order spectral values. The second sum is calculated over a frequency band lying above high frequency EEG activity (k>2 and n>1). A state index is then formed, which is dependent on the at least one parameter and indicative of the cerebral state of the subject. The first and second parameters may be used in the Bispectral Index (BIS™) algorithm.

34 Claims, 3 Drawing Sheets

MONITORING OF THE CEREBRAL STATE OF A SUBJECT

FIELD OF THE INVENTION

The present invention relates generally to the monitoring of the cerebral state of a subject. The invention finds a typical application in a monitoring process in which the sedation or hypnosis of a patient is assessed by determining a so-called Bispectral Index (BIS™).

BACKGROUND OF THE INVENTION

Neuromonitoring is a subfield of clinical patient monitoring focused on measuring various aspects of brain function and on changes therein caused by drugs commonly used to induce and maintain anesthesia in an operation room or sedation in patients under critical or intensive care.

Electroencephalography (EEG) is a well-established method for assessing brain activity. When measurement electrodes are attached on the skin of the skull surface, the weak biopotential signals generated in the pyramid cells of the cortex may be recorded and analyzed. The EEG has been in wide use for decades in basic research of the neural systems of the brain as well as in the clinical diagnosis of various central nervous system diseases and disorders.

Electromyography (EMG) is a method for recording electrical biopotentials of muscles. In an EMG measurement, the electrodes are attached onto the surface of the skin overlying a muscle. When a biopotential signal is recorded from the forehead of a subject, the recorded signal indicates both the activity of the facial muscles (fEMG) and the brain (EEG).

One of the special applications of the EEG, which has received attention recently, is the use of a processed EEG signal for objective quantification of the amount and type of brain activity for the purpose of determining the level of consciousness of a patient. In its simplest form, the utilization of an EEG signal allows the automatic detection of the alertness of an individual, i.e. if he or she is awake or asleep. This has become an issue of increased interest, both scientifically and commercially, in the context of measuring the depth of unconsciousness induced by anesthesia during surgery.

Another important component of balanced anesthesia is analgesia which means prevention of pain reactions of a patient by administration of pain medication. Adequate analgesia reduces surgical stress and there is firm evidence that it decreases postoperative morbidity. Awareness during surgery with insufficient analgesia may lead to a post-traumatic stress disorder. Low quality pre- and intra-operative analgesia makes it difficult to select the optimal pain management strategy later on. More specifically, it may cause exposure to unwanted side effects during the recovery from the surgery. If the anesthesia is too light and involves insufficient hypnosis, it may cause traumatic experiences both for the patient and for the anesthesia personnel. From an economical point of view, if the anesthesia is too deep, it may cause increased perioperative costs through extra use of drugs and time, and extend the time required for post-operative care.

Virtually every patient being cared for in an intensive care unit, for example, receives some form of sedation. However, the control of the depth of the sedation administered to a patient is still problematic, and therefore oversedation and undersedation are both common occurrences in intensive care units. At present, monitoring the level of sedation is mainly handled by using subjective observations from the patient. Various sedation assessment scales have been developed for subjectively assessing the level of sedation, the Ramsay Score being one of the most widely used tools for this purpose. Inappropriate sedation can lead to an adverse clinical outcome and reduce treatment efficacy in critical care settings. Oversedation may cause various complications, such as cardiovascular instability, and it may also increase the length of stay in the hospital and prolong the usage time of expensive facilities, such as the intensive care unit. Undersedation, in turn, may result in patient anxiety and agitation, which can further interfere with care, especially with that of neurological patients, and result in harm to the patient and the nursing staff.

The depth of hypnosis is not directly measurable. Therefore, drug delivery systems have to derive the level of hypnosis from a surrogate signal or from indirectly measured parameters. The most common and popular surrogate signal for this purpose is the EEG, from which several parameters may be determined. The basic reason for the insufficiency of a single parameter is the variety of drugs and the complexity of the drug effects on the EEG signal in human brains. However, during the past few years, some commercial validated devices for measuring the level of consciousness and/or awareness in clinical set-up during anesthesia or sedation have become available. Such devices, which are based on a processed EEG signal and examine the signal as a whole with its multiple features, are marketed by GE Healthcare Finland Oy, Kuortaneenkatu 2, FIN-00510 Helsinki (Entropy Index) and by Aspect Medical Systems, Inc., 141 Needham Street, Newton, Mass. 02464, U.S.A. (Bispectral Index, BIS™).

The above devices utilize spectral analysis, which is a traditional technique in EEG signal monitoring. A spectral analysis based on multiple orders of the spectrum is commonly referred to as a higher-order spectral analysis. Power spectrum is a second order spectrum, bispectrum a third order spectrum, and trispectrum a fourth order spectrum, for example. The nomination arises from statistics, where the (k−1)-dimensional Fourier transform of the k-th order cumulant of a given time series produces the k-th order spectrum.

The advantages of a spectral analysis of an order higher than two are, for example, the ability to describe non-Gaussian processes and to preserve phase, immunity to Gaussian noise, and the ability to characterize nonlinearities. Irrespective of the spectral order, a spectral analysis may be performed based on various techniques. While Fourier transform is an efficient method computationally, other methods, like autoregressive modeling, for example, may also be used. Further information about higher-order spectral analysis can be found in Athina P. Petropulu, *Higher-Order Spectral Analysis*, The Biomedical Engineering Handbook (Edit. Joseph D. Bronzino), Second Edition, Vol. 1, pp. 57.1-57.17, and references therein.

In addition to the EEG signal data, EMG signal data obtained from facial muscles (fEMG) of the forehead is used for monitoring purposes during anesthesia and intensive care. Recovering facial muscle activity is often the first indicator of the patient approaching consciousness. When this muscle activity is sensed by electrodes placed appropriately, it provides an early indication that the patient is emerging from anesthesia. Similarly, these electrodes can sense pain reactions when the anesthesia is not adequate due to inadequate analgesia. So, the EMG signals give an early warning of arousal and may also be indicative of inadequate analgesia.

In connection with anesthesia, the patient is administered hypnotic, analgesic, and neuromuscular blocking agents. However, a certain drug is not normally a pure hypnotic or a pure analgesic, but the drugs normally have additive effects. The anesthetics, i.e. drugs used to produce anesthesia, may also be divided into different groups according to the site of their action. This is discussed briefly in the following.

Glutamate is the most important excitatory transmitter in the central nervous system. Glutamate is involved in sensory processing, motor control and higher cortical functions, including memory and learning. Glutamate acts both through ligand gated ion channels (ionotropic receptors) and second messenger (here G-protein) coupled (metabotropic) receptors. Ionotropic glutamate receptors can be divided into three groups: AMPA receptors, NMDA receptors, and kainate receptors.

Gamma-aminobutyric acid (GABA) is the main inhibitory neurotransmitter in the central nervous system. GABA is involved in 20 to 50 percent of brain synapses, depending on the brain area. There are three types of GABA receptors: $GABA_A$ and $GABA_C$ receptors, which are associated with chloride channels, and $GABA_B$ receptors, which are G-protein coupled (metabotropic) receptors. Binding of GABA to a $GABA_A$ receptor increases the permeability to chloride ion which leads to hyperpolarization of the neuronal membrane and to increased inhibition. A $GABA_A$ receptor contains, for example, the following binding sites: GABA, benzodiazepine and barbiturate sites.

Anesthetics bind to specific, saturable binding sites (i.e. receptors) typically on the cell membrane. Effects of anesthetics are receptor-mediated. General anesthesia may be produced by different mechanisms: anesthetics may act at different receptors or they may act at different sites of the same receptor.

At present, most of the anesthetics act primarily through $GABA_A$-receptors. These drugs, also termed GABA agonistic agents, potentiate the actions of GABA causing hyperpolarization of the neuronal membrane. This action is common to barbiturates, propofol, etomidate, and steroid anesthetics, for example, and probably also to inhalational anesthetics.

Although most anesthesias are today conducted by GABA agonistic agents, another group of anesthetics is also used, which affects the N-methyl-D-aspartate (NMDA) receptors thereby attenuating excitatory neurotransmission. These drugs, also termed NMDA antagonists in this context, inhibit the actions of glutamate by blocking the NMDA receptors. This action is common to phencyclidine derivatives, like ketamine and S-ketamine, and to nitrous oxide and xenon, for example.

As noted above, one commonly used commercial tool for assessing the level of sedation or hypnosis is the Bispectral Index, BIS™. The BIS algorithm involves the calculation of three parameters, Beta Ratio, SynchFastSlow, and Burst Suppression Ratio, and the resulting index is a combination of the three parameters. Some of the techniques for analyzing EEG signals in an effort to determine the depth of anesthesia as well as the principles of the BIS algorithm are described in Ira J. Rampil, *A Primer for EEG Signal Processing in Anesthesia*, Anesthesiology, Vol. 89(4) October 1998, pp. 980-1002.

At present, the processes utilizing raw EEG signal data for monitoring a patient under sedation or anesthesia inherently assume either that during anesthesia the EMG activity is either very low and thus negligible or that the frequencies of the EMG spectrum are above the frequencies of brain activities, whereby the EMG components can be separated by methods of signal processing or spectral analysis from the EEG signal components contained in the signal data. This causes no problems in connection with the use of GABA agonistic agents, since the administration of GABA agonistic agents results in a more ordered EEG signal with spectral power concentrated onto the low frequencies. In this context, low frequencies refer to frequencies below about 20 Hz, while high frequencies refer to frequencies above about 20 Hz. A more ordered EEG signal will be the result also when NMDA antagonists are administered. However, NMDA antagonists produce both low and high frequency EEG activity, which causes BIS-based patient monitors to produce false indications and thus renders the said monitors unreliable when the said drugs are administered to the patient.

The present invention seeks to alleviate or eliminate the above-mentioned drawback and to bring about a method by means of which the BIS algorithm may be used in connection with the administration of NMDA antagonists.

SUMMARY OF THE INVENTION

The present invention seeks to improve the reliability and thus also to extend the applicability of existing patient monitors based on the determination of the known Bispectral Index, BIS™. The invention further seeks to provide a method and apparatus, which are applicable for determining a reliable measure of the depth of anesthesia or sedation when NMDA antagonists are involved in producing anesthesia or sedation.

The unreliability of the BIS-based patient monitors in connection with the administration of NMDA antagonists is caused by the fact that two of the BIS parameters, so-called Beta Ratio and SynchFastSlow, which normally decrease as the patient approaches unconsciousness produced by GABA agonistic agents, remain erroneously high or decrease only moderately, respectively, when NMDA antagonists are used. The reason for this erroneous operation is the high frequency EEG activity induced by NMDA antagonists. In the present invention, the operation of a BIS-based monitoring process is modified by replacing the said parameters by parameters which behave consistently regardless of whether GABA agonistic agents or NMDA antagonists are used. The conventional Beta Ratio parameter is replaced by a parameter indicative of the sum of spectral values of the signal data in a frequency band lying above high frequency EEG activity, while the conventional SynchFastSlow parameter, which is derived from the ratio of two sums of bispectral values, is replaced by a parameter indicative of the relative magnitudes of a first sum of k-th order spectral values and a second sum of n-th order spectral values, wherein the second sum is calculated over a frequency range lying above high frequency EEG components. The values of k and n are typically the same, although this may not always be the case. Both novel parameters behave consistently regardless of whether GABA agonistic agents or NMDA antagonists are used, and each of them may also be used as the sole indicator of the depth of anesthesia or sedation.

The parameter replacing the conventional Beta Ratio may be calculated based on a power spectral, bispectral or any other higher order spectral analysis, whereas the parameter replacing the SynchFastSlow may be calculated based on a bispectral or any other higher order spectral analysis. Furthermore, although the spectral orders of the first and second sums are typically the same, the said sums may also be calculated employing different spectral orders. More specifically, the spectral order corresponding to the second sum may be lower than that corresponding to the first sum. In other words, the said parameters may be calculated based on a k-th order spectral analyses, where k>1 applies to the parameter replacing the conventional Beta Ratio parameter and k>2 applies to the first sum and k>1 to the second sum related to the parameter replacing the conventional SynchFastSlow parameter. The selection of the spectral order(s) for one parameter does not affect the selection for the other parameter, i.e. the values of k may be selected independently for each parameter, provided that the above limitations are obeyed. As noted above, in this context k-th order spectral values refer to values calculated in a (k−1)-dimensional space of frequency.

Thus one aspect of the invention is providing a method for monitoring the cerebral state of a subject. The method includes the steps of obtaining physiological signal data from a subject, the physiological signal data including EEG signal components, and deriving at least one of a first and second parameters from the physiological signal data, wherein the first parameter is indicative of the sum of spectral values of the physiological signal data in a first frequency band lying above high frequency EEG activity and the second parameter is indicative of the relative magnitudes of a first sum of k-th order spectral values and a second sum of n-th order spectral values, wherein the second sum is calculated over a second frequency band lying above high frequency EEG activity, and wherein k is an integer greater than two and n is an integer greater than one. The method further includes forming a state index which is dependent on the at least one parameter derived in the deriving step, the state index being indicative of the cerebral state of the subject.

Another aspect of the invention is that of providing an apparatus for monitoring the cerebral state of a subject. The apparatus comprises means for receiving physiological signal data from a subject, the physiological signal data including EEG signal components, and first calculation means for deriving at least one of a first and second parameters from the physiological signal data, wherein the first parameter is indicative of the sum of spectral values of the physiological signal data in a first frequency band lying above high frequency EEG activity and the second parameter is indicative of the relative magnitudes of a first sum of k-th order spectral values and a second sum of n-th order spectral values, wherein the second sum is calculated over a second frequency band lying above high frequency EEG activity, and wherein k is an integer greater than two and n is an integer greater than one. The apparatus further comprises second calculation means for forming a state index which is dependent on the at least one parameter, the state index being indicative of the cerebral state of the subject.

The invention enables correct and reliable measures of the depth of anesthesia or sedation, such as BIS values, to be determined whenever NMDA antagonists are used to produce the anesthesia, regardless of whether NMDA antagonists are used with or instead of GABA agonistic agents. Furthermore, the invention allows reliable estimates of the level of consciousness to be obtained within a wide range of consciousness levels.

In one embodiment of the invention, the novel parameters are used together with a burst suppression index to obtain a reliable and consistently behaving measure of the depth of anesthesia or sedation.

In another embodiment of the invention, the second parameter is indicative of the ratio of the first and second sums. However, other quantifications for the relative magnitudes of the two sums may also be used.

A further aspect of the invention is that of providing a computer program product by means of which known patient monitoring devices may be upgraded and thus their applicability extended. The program product includes a first program code portion for receiving physiological signal data obtained from a subject, the physiological signal data including EEG signal components; and a second program code portion configured to derive at least one of a first and second parameters from the physiological signal data, wherein the first parameter is indicative of the sum of spectral values of the physiological signal data in a first frequency band lying above high frequency EEG activity and the second parameter is indicative of the relative magnitudes of a first sum of k-th order spectral values and a second sum of n-th order spectral values, wherein the second sum is calculated over a second frequency band lying above high frequency EEG activity, and wherein k is an integer greater than two and n is an integer greater than one.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 1 to 7 in the appended drawings, wherein.

DETAILED DESCRIPTION OF THE INVENTION

Figure 1:
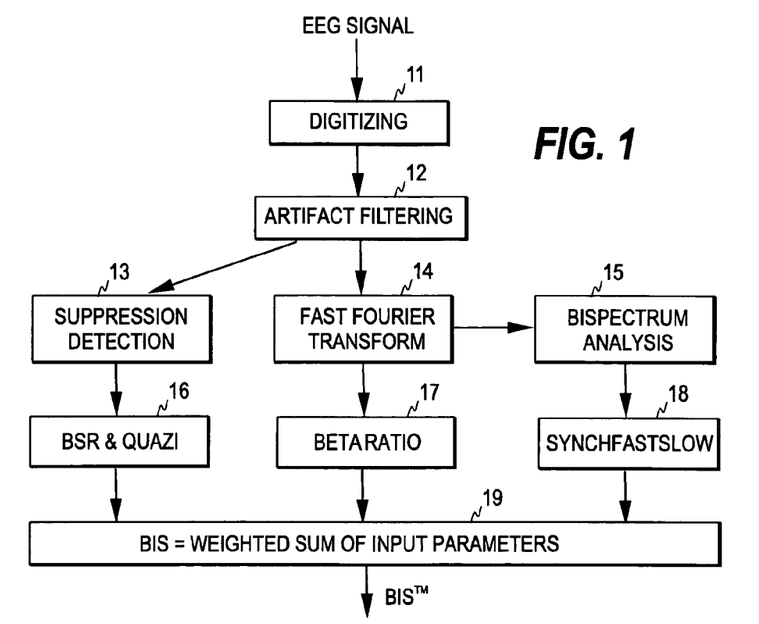
FIG. 1 illustrates the calculation of the conventional Bispectral Index, BIS™.

As the present invention finds a typical application in the known BIS algorithm, the relevant parts of the determination of the BIS are first discussed briefly with reference to FIG. 1, which illustrates the steps of the BIS algorithm. A more detailed discussion of the BIS algorithm can be found in the above-mentioned article by Ira J. Rampil, which is incorporated herein by reference in its entirety.

The EEG signal measured from a patient is first digitized (step 11), and the sampled EEG signal is filtered to exclude high- and low-frequency artifacts (step 12). As is common in the art, the digitized signal samples are processed as sets of sequential signal samples representing finite time blocks or time windows, commonly termed "epochs".

The BIS involves the calculation of three parameters: Burst Suppression Ratio, Beta Ratio, and SynchFastSlow, and the resulting index is a combination of the three parameters.

If an incoming epoch is artifact-free or deemed repaired, a degree of burst suppression is calculated using two separate algorithms, BSR and QUAZI. (steps 13 and 16). Burst suppression is a certain pattern of EEG, which is characterized by alternating periods of normal to high voltage activity that changes to low voltage or even isoelectricity (suppressed state). The burst suppression pattern may be induced, for example, by large doses of anesthetics. Therefore, the BSR and QUAZI values are used to detect deep anesthesia in the BIS algorithm. The BSR indicates the fraction of the epoch length where the EEG is in a suppressed state. The QUAZI algorithm provides a similar suppression index, but it is designed to detect burst suppression in case the baseline voltage wanders, which may confuse the BSR algorithm. The final burst suppression index obtained from step 16 may be the combination of the BSR and QUAZI values.

The Beta Ratio, calculated at step 17, is a frequency domain-based parameter. Therefore, a preceding transform (step 14) is required to calculate the frequency components of the epochs. The Beta Ratio is calculated as the logarithm of the ratio of the EEG signal power in two empirically derived frequency bands, i.e. Beta Ratio=log(P1/P2), where P1 is the sum of the spectral power in a frequency band extending from 30 to 47 Hz and P2 is the sum of the spectral power in a frequency band extending from 11 to 20 Hz. The Beta Ratio is supposed to detect light levels of sedation or anesthesia.

The SynchFastSlow parameter is derived from a bispectrum analysis (step 15 and 18), and it is indicative of the degree of phase coupling in the EEG signal. The degree of phase coupling in the EEG signal increases as the anesthesia deepens. The said parameter is defined as the logarithm of the ratio of the sum of all bispectrum peaks in the frequency range from 0.5 to 47 Hz over the sum of the bispectrum in the frequency range from 40 to 47 Hz. The SynchFastSlow parameter itself is useful for tracking surgical anesthesia.

The different parameters are weighted according to their range of best performance to obtain the final BIS value (step 19). Different parameters thus dominate the resulting BIS as the anesthesia increases. The Beta Ratio is weighted most heavily during light sedation, while the SynchFastSlow is weighted most heavily during surgical anesthesia. Therefore, when the patient approaches unconsciousness the Beta Ratio decreases and the BIS algorithm starts to put more weight on the SynchFastSlow parameter.

However, while the BIS works well with GABA agonistic agents, it fails with NMDA antagonists, like ketamine. The reason is that the NMDA antagonists induce high frequency EEG activity that affects both the Beta Ratio and the SynchFastSlow parameters. The high frequency EEG activity gives rise to high values of the Beta Ratio unless the patient is deeply anesthetized and prevents the SynchFastSlow from decreasing normally as the patient approaches unconsciousness. In the present invention, the two parameters may be replaced by novel parameters which behave consistently regardless of whether GABA agonistic agents or NMDA antagonists are used. The replacement of the Beta Ratio is discussed first.

Figure 2:
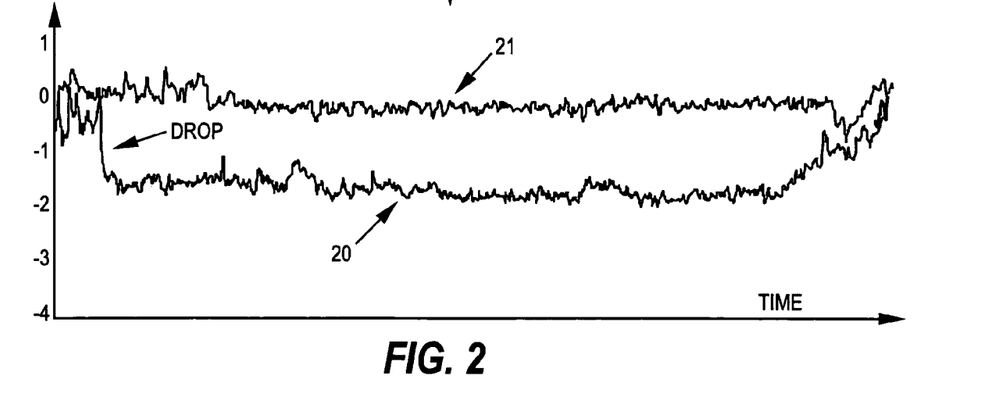
FIG. 2 illustrates the behavior of the Beta Ratio parameter of the BIS algorithm during propofol and ketamine anesthesias.

As noted above, the Beta Ratio remains erroneously high if high frequency EEG activity produced by NMDA antagonists is present, as a result of which the BIS algorithm is incapable of increasing the weight of the SynchFastSlow parameter. This is illustrated in the example of FIG. 2, which shows the behavior of the Beta Ratio during a propofol anesthesia (curve 20) and during a ketamine anesthesia (curve 21). As can be seen from the figure, the Beta Ratio drops when the patient loses consciousness, but the drop occurs only in the propofol anesthesia. In the ketamine anesthesia, the Beta Ratio may remain high throughout the anesthesia.

In the present invention, the inconsistent behavior of the Beta Ratio is eliminated by replacing the Beta Ratio by another parameter, which is here termed the EMG Ratio. In the EMG Ratio, the numerator represents pure EMG power regardless of whether GABA agonistic agents or NMDA antagonists are involved. Therefore, the numerator represents the sum of spectral values in a frequency band whose lower limit is above the EEG frequencies regardless of whether NMDA antagonists are used or not. The lower limit of the said frequency band is therefore typically greater than 70 Hz, preferably about 105 Hz. The upper limit of the said band may be between 115 Hz and 150 Hz, for example. As to the denominator of the EMG Ratio, it is advantageous to use a power value, which is somewhat similar to the denominator of the Beta Ratio. This is because the power in the band extending from 11 Hz to 20 Hz increases when the patient reaches unconsciousness and decreases during arousal from anesthesia. Additionally, the frequency band extending from 11 Hz to 20 Hz is not sensitive to eye movements. Because the signal power is subject to inter-patient variability, it is advantageous to utilize a ratio of the EMG and EEG powers rather than the absolute EMG power as such.

A preferred implementation of the EMG Ratio is therefore obtained by dividing the sum of spectral values in a pure EMG band by the sum of spectral values in a pure EEG band. The EMG Ratio may therefore correspond to the ratio $(P_{105-145})/(P_{11-20})$, for example, where $P_{A-B}$ is the sum of spectral values in a band extending from A Hz to B Hz. Because the frequency bands of EEG and EMG overlap in the range of 20 to 100 Hz (depending on the anesthetic used), a percentual EMG Ratio, such as $(P_{105-145})/(P_{1-145})$, is a less accurate estimate for the depth of hypnosis than a ratio where the denominator represents the sum of spectral values in a pure EEG band. However, any appropriate denominator may be used to obtain a normalized parameter, which is indicative of the sum of the spectral values of the signal data in a frequency band lying above high EEG activity.

In preferred embodiments of the invention, the spectral values for the EMG Ratio are derived from a power spectrum. The Fast Fourier Transform, for example, is a computationally effective algorithm for this purpose, but other techniques, like autoregressive modeling, may also be used. Alternatively, the EMG Ratio may be calculated straight from the time-domain signal, by utilizing appropriate filters. The EMG Ratio may also be calculated from the spectra obtained from any other higher-order spectral analysis, like bispectrum, for example. In this alternative the EMG Ratio may correspond, for example, to the ratio $(B_{105-145,105-145})/(B_{11-20,11-20})$, where $(B_{A-B,A-B})$ is the sum of bispectral values in a frequency range extending from A Hz to B Hz. In practice, the two-dimensional frequency space of a bispectrum is symmetrical over axis $B_{c,c}$, so summation over only one triangular space is needed. Utilization of a bispectral analysis in the calculation of the EMG Ratio is advantageous in the sense that such an analysis is indicative of both the non-linear phase coupling between different EEG pacemaker elements and the proportional EEG signal power on two frequency bands.

Due to the large variations in the above-mentioned power ratio during anesthesia, the usability of the EMG Ratio may be improved if the final EMG Ratio parameter is calculated as the logarithm of the above-mentioned ratio of the spectral values sums (similarly as the logarithm is used for the Beta Ratio). It is also to be noted here that instead of the above-mentioned ratios their inverses may be calculated as well. In other words, the inverses of the above parameters are also indicative of the sum of the spectral values of the signal data in a frequency band lying above high EEG activity. The logarithm may be derived irrespective of whether the above-mentioned ratios or their inverses are used. Therefore, the EMG Ratio may be any parameter which is in a predetermined manner dependent on the above-mentioned spectral sum ratios or their inverses.

Figure 3:
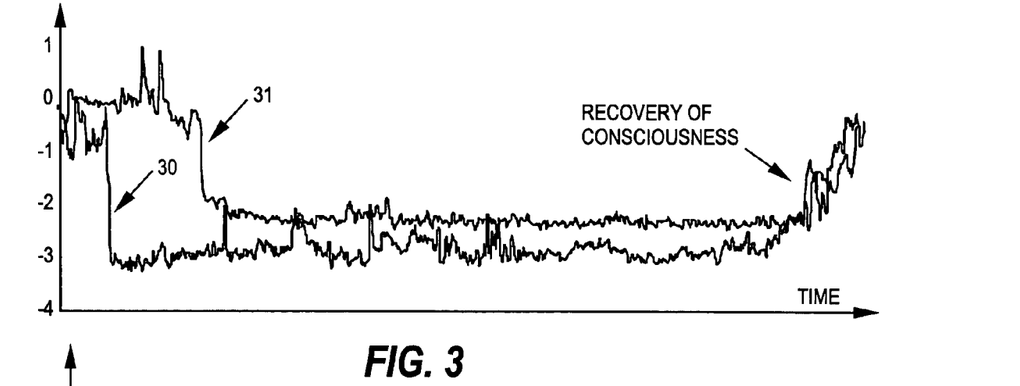
FIG. 3 illustrates the behavior the EMG Ratio parameter of the invention during a propofol and ketamine anesthesias when the EMG Ratio is calculated from power spectrum.
Figure 4A:
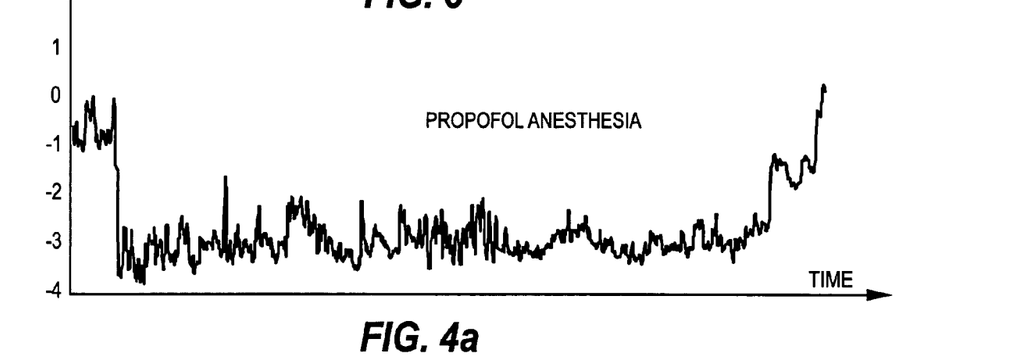
FIGS. 4a and 4b illustrate the behavior the EMG Ratio parameter of the invention during a propofol and ketamine anesthesias, respectively, when the EMG Ratio is derived from a bispectrum analysis.
Figure 4B:
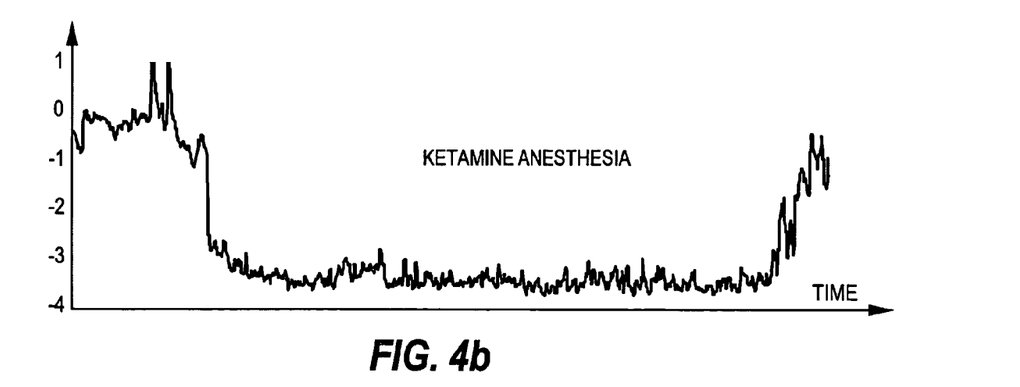

FIG. 3 illustrates the behavior of the EMG Ratio of the invention during the propofol and ketamine anesthesias of FIG. 2. Curve 30 represents the propofol anesthesia, while curve 31 represents the ketamine anesthesia. Both curves represent the logarithm of the above-mentioned preferred power ratio, i.e. the curve values equal to $\log((P_{105\text{-}145})/(P_{11\text{-}20}))$. FIGS. 4a and 4b in turn illustrate the behavior the EMG Ratio during the said propofol and ketamine anesthesias, respectively, when the EMG Ratio is derived from a bispectrum analysis and the curve values are equal to $\log((B_{105\text{-}145,105\text{-}145})/(B_{11\text{-}20,11\text{-}20}))$. As can be seen from the figures, the EMG Ratio behaves consistently regardless of the type of the anesthetic and regardless of whether the ratio of the spectral sums is derived from power spectral or bispectral values, i.e. there is a clear drop in each curve of the EMG Ratio when the patient reaches unconsciousness and each curve also clearly indicates the recovery of consciousness.

Although the invention is primarily intended for improving the BIS algorithm, the EMG Ratio may also be used without the burst suppression index (BSR/QUAZI) and the bispectrum value (the traditional SynchFastSlow or the modified SynchFastSlow described below). More specifically, as the EMG Ratio is a reliable indicator of the depth of hypnosis at light levels of anesthesia, one embodiment of the invention involves the use of the EMG Ratio as the sole indicator of the depth of hypnosis at light levels of anesthesia or sedation, which refers to levels 5 to 2 in the Observer's Assessment of Alertness and Sedation (OAAS) scale to obtain an indication of the level of consciousness. Outside this area, any other known mechanism may be used, if necessary. The OAAS is a scale that defines the level of consciousness based on a patient's response to external stimuli. In this embodiment, the calculation of the measure of the depth of anesthesia or sedation thus involves steps 11, 12, 14, and 17 of FIG. 1, the EMG Ratio being now calculated at step 17.

It must also to be noted that if the invention is used in connection with a BIS algorithm, the burst suppression index may be the conventional Burst Suppression Ratio or an index derived by any other applicable technique. The used technique may be, for example, as described in Mika Särkelä et al., *Automatic analysis and monitoring of burst suppression in anesthesia*, Journal of Clinical Monitoring and Computing, Vol. 17. 2002, pp. 125-134.

As discussed above, the high frequency EEG activity induced by NMDA antagonists may also give rise to inconsistent behavior of the conventional SynchFastSlow parameter. This is eliminated by replacing the said parameter by a parameter which is indicative of the ratio of two sums of k-th order spectral values, where k is an integer equal to or greater than 3. In this ratio, the denominator is derived from a frequency band lying above high frequency EEG activity, whereas the numerator of the ratio may be calculated over a frequency band that covers roughly the frequencies used in the conventional SynchFastSlow parameter, but preferably also the high frequency EEG activity.

The modified SynchFastSlow parameter may thus be calculated, for example, as the ratio $(B_{0.5\text{-}93.5,0.5\text{-}93.5})/(B_{79.5\text{-}93.5,79.5\text{-}93.5})$, where $(B_{A\text{-}B,A\text{-}B})$ is the sum of bispectral values in the frequency range extending from A Hz to B Hz. Here, the numerator covers all relevant EEG signal components also in case of NMDA antagonists. Alternatively, the frequency range corresponding to the numerator may be narrower and fail to cover high frequency EEG components. For example, the numerator may be calculated over the conventional frequency range of 0.5 to 47 Hz.

As in the case of the EMG Ratio, the inverses of the above-mentioned ratios may be used for the modified SynchFastSlow and the logarithm of the ratios or their inverses may also be used to enhance the usability of the parameter. The modified SynchFastSlow parameter is thus in a predetermined manner dependent on the above-mentioned ratios or their inverses. If the EMG Ratio and the modified SynchFastSlow are used to replace the Beta Ratio and the SynchFastSlow parameters, respectively, in the BIS algorithm, the logarithms may also be calculated in the weighting step (step 19 in FIG. 1). In this case, the logarithm operation is part of the weight given to each parameter.

Figure 5:
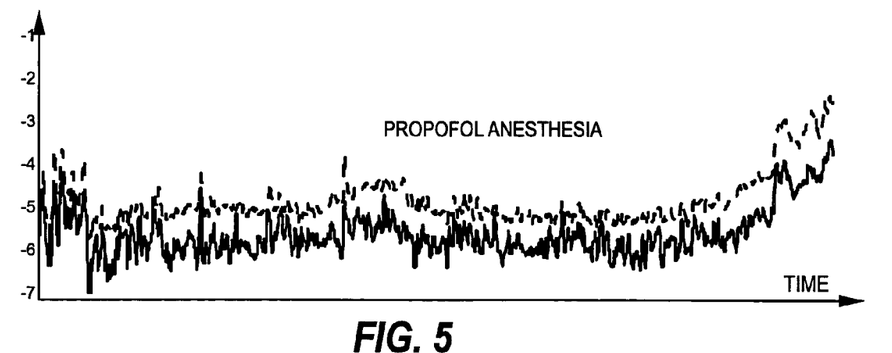
FIG. 5 illustrates the behavior of the conventional SynchFastSlow parameter and the modified SynchFastSlow parameter of the invention during a propofol anesthesia.
Figure 6:
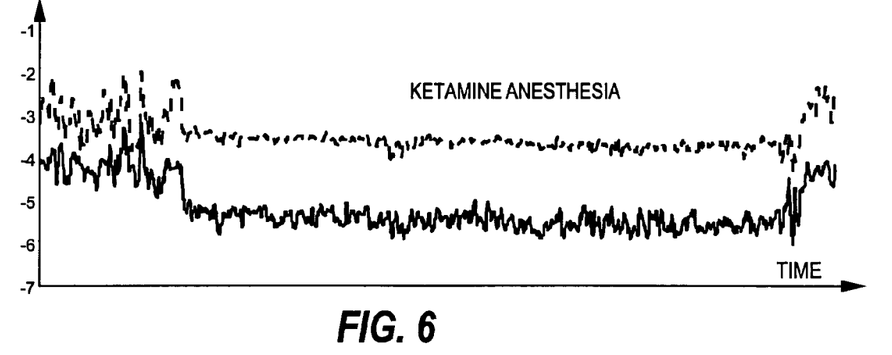
FIG. 6 illustrates the behavior of the conventional SynchFastSlow parameter and the modified SynchFastSlow parameter of the invention during a ketamine anesthesia.

FIG. 5 illustrates the behavior of the conventional SynchFastSlow and the modified SynchFastSlow parameter of the invention during a propofol anesthesia, while FIG. 6 illustrates the behavior of the same parameters during a ketamine anesthesia. In both figures, the dashed line represents the conventional SynchFastSlow parameter, while the solid line represents the modified SynchFastSlow parameter of the invention (calculated as the logarithm of $(B_{79.5\text{-}93.5,79.5\text{-}93.5})/(B_{0.5\text{-}93.5,0.5\text{-}93.5})$). In FIG. 5, the curves include a lot of eye movements, therefore the transfer to an unconscious state is not as clear as in the previous figures. However, what is important in FIG. 5 is that the traditional and the modified SynchFastSlow parameters behave in a similar manner. Since the values shown in the y-axis of FIGS. 5 and 6 are comparable, the curves also indicate that the modified SynchFastSlow parameter of the invention behaves consistently regardless of whether propofol or ketamine is involved, while the values of the conventional SynchFastSlow parameter remain substantially higher in case of the ketamine anesthesia than in case of propofol anesthesia.

As the EMG Ratio, the modified SynchFastSlow parameter of the invention may also be used without the other BIS parameters as the sole indicator of the depth of hypnosis or sedation. Furthermore, provided that the artifacts caused by eye movements are eliminated from the signal, the modified SynchFastSlow may be used as the sole indicator for a range of consciousness levels, which is wider than the corresponding range for the EMG Ratio. When the modified SynchFastSlow parameter operates as the only indicator of the depth of anesthesia or sedation, the calculation of the said parameter thus involves steps 11, 12, 14, 15, and 18 of FIG. 1, the modified SynchFastSlow parameter now being calculated at step 18.

If the EMG Ratio or the modified SynchFastSlow parameter is used as the sole indicator of the depth of anesthesia or sedation, the final index value is not necessarily equal to the value of the indicator but the said value may still be transformed to an output scale for enhancing usability, for example. Generally, the final index has a predetermined relationship with the above parameter(s).

In one embodiment of the invention, the two spectral sums forming the numerator and denominator of the modified SynchFastSlow parameter may be determined by employing power spectral values for the spectral sum derived from a frequency band lying above high frequency EEG activity. In other words, the spectral order is not necessarily the same for the two spectral sums but the spectral order of the sum calculated over the frequency band lying above high frequency EEG activity may be lower than the spectral order of the other sum. Furthermore, it is not necessary that the modified SynchFastSlow parameter of the invention is indicative of the ratio of two spectral sums, but other quantifications may also be used, which are indicative of the relative magnitudes of the two sums. For example, the two sums may be deducted from each other to obtain such a quantification.

Figure 7:
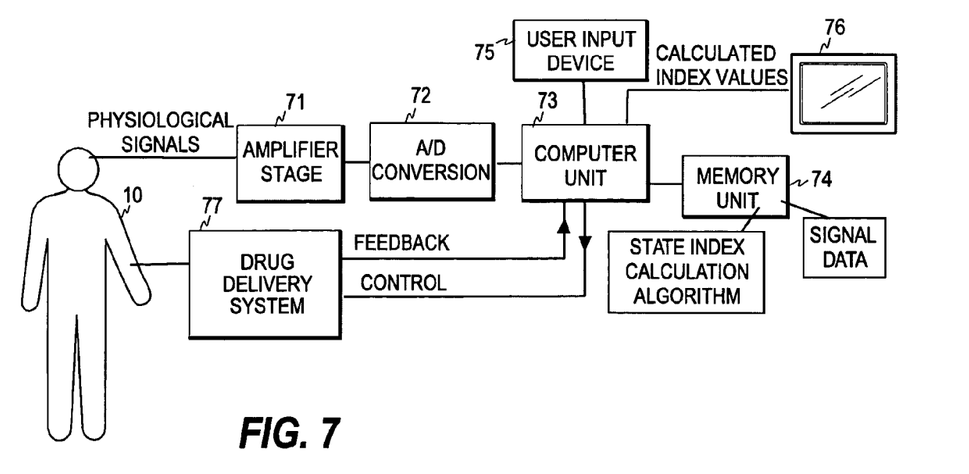
FIG. 7 illustrates one embodiment of the system according to the invention.

FIG. 7 illustrates one embodiment of the system or apparatus according to the invention. The physiological signal(s) obtained from one or more sensors attached to a patient 10 are supplied to an amplifier stage 71, which amplifies the signal(s) before they are sampled and converted into digitized format in an A/D converter 72. The digitized signals are supplied to a computer unit 73 which may comprise one or more processors. As noted above, the signal data measured from the patient is typically EEG signal data, which is measured through electrodes applied to the forehead of the patient. The electrodes also receive EMG signal data from the patient.

The computer unit is provided with a memory or database 74 holding the digitized signal data obtained from the sensor(s). The memory or database may also store the respective calculation algorithm, such as the BIS algorithm, which now includes the determination of at least one of the EMG Ratio and the modified SynchFastSlow parameters. Using the algorithm and the signal data the computer unit continuously updates the final index, such as the BIS, and displays the result on the screen of a monitor 76. Although one computer unit or processor may perform the above steps, the processing of the data may also be distributed among different units/processors (servers) within a network, such as a hospital LAN (local area network). The apparatus of the invention may thus also be implemented as a distributed system.

The computer unit may further act as a controlling entity controlling the administration of the drugs from the delivery system 77 to the patient. The computer unit may also supply the index values to another computer unit or microprocessor (not shown), which then acts as the controlling entity controlling the drug delivery system. The said controlling entity may be provided with the control data needed for the administration, such as the pharmacodynamic and pharmacokinetic properties of the drugs to be administered. The drug delivery system may comprise separate delivery units for one or more drugs to be administered, such as delivery unit for an analgesic drug and/or a delivery unit for a hypnotic drug.

The computer unit may also act as decision-support tool for the physician, such as an anesthesiologist, who may control the operation of the drug delivery system through an appropriate user input device 75, such as a keyboard or a bar code reader. Various parameters possibly needed in the calculation of the state index values may also be supplied through the input device, if the computer unit has no access to such data.

A conventional patient monitor may also be upgraded to enable the monitor to determine an index that remains consistent regardless of the type of drugs administered to the patient. Such an upgrade may be implemented by delivering to the patient monitor a software module that enables the device to control the calculation of the state index in the above-described manner. The software module may be delivered, for example, on a data carrier, such as a CD or a memory card. The software module, which may be provided with an interface to the memory storing the signal data measured by the patient monitor, may be a so-called plug-in module that adds the novel features of the invention to a conventional patient monitor or a new version of the software, which replaces the existing software of the patient monitor. For example, if the existing BIS software is implemented in modules corresponding to the various parameters, the module determining the Beta Ratio and optionally the module determining the SynchFastSlow need to be updated. In this case the plug-in module includes a first interface for receiving signal data values, a second interface for outputting the calculated EMG Ratio values to a module that defines the weighted sum of the parameters, and a third interface for outputting the values modified SynchFastSlow to the said module, if the modified SynchFastSlow is also calculated.

Although the invention was described above with reference to the examples shown in the appended drawings, it is obvious that the invention is not limited to these, but may be modified by those skilled in the art without departing from the scope and spirit of the invention. The detection mechanism of the invention may also be used outside the operation room for assessing the cerebral state of the patient.

The invention claimed is:

1. A method for monitoring the cerebral state of a subject, the method comprising the steps of:
   obtaining physiological signal data from a subject, the physiological signal data including EEG signal components;
   deriving, using a computer unit, a first parameter from the physiological signal data, wherein the first parameter is indicative of the relative magnitudes of a first sum of k-th order spectral values and a second sum of n-th order spectral values, wherein the second sum is calculated over a first frequency band lying above high frequency EEG activity and consisting mostly of EMG activity, and wherein k is an integer greater than two and n is an integer greater than one; and
   forming a state index which has a predetermined relationship with the first parameter derived in the deriving step, the state index being indicative of the cerebral state of the subject.

2. A method according to claim 1, wherein
   the deriving step further includes deriving a first parameter, wherein the first parameter is indicative of the sum of spectral values of the physiological signal data in a second frequency band lying above high frequency EEG activity and consisting mostly of EMG activity, and
   the forming step includes deriving the state index, in which the state index is dependent on the first parameter and the second parameter.

3. A method according to claim 1, further comprising a step of administering at least one drug to the subject, wherein the at least one drug belongs to a group of N-methyl-D-aspirate (NMDA) antagonists.

4. A method according to claim 2, wherein
   the method further comprises a step of deriving a burst suppression index indicative of burst suppression in the physiological signal data; and
   the forming step includes forming a weighted sum of the first parameter, the second parameter, and the burst suppression index.

5. A method according to claim 2, wherein the second parameter is indicative of the sum of power spectral values of the physiological signal data in the second frequency band.

6. A method according to claim 2, wherein the second parameter is indicative of the sum of bispectral values of the physiological signal data in the second frequency band.

7. A method according to claim 2, wherein the second parameter is indicative of the sum of k-th order spectral values of the physiological signal data in the second frequency band where k for the spectral values of the physiological signal data in the second frequency band is an integer greater than three.

8. A method according to claim 1, wherein the k-th and n-th order spectral values are bispectral values.

9. A method according to claim 1, wherein the first parameter is indicative of the ratio of the first and second sums.

10. A method according to claim 9, wherein the first frequency band extends from a frequency of about 80 Hz to a frequency of about 95 Hz.

11. A method according to claim 10, wherein the first sum is calculated over a frequency band extending from a frequency of about 0.5 Hz to a frequency of about 95 Hz.

12. A method according to claim 9, wherein the deriving step further includes calculating the logarithm of the ratio.

13. A method according to claim 5, wherein the deriving step includes the sub-steps of:
   calculating, based on the physiological signal data, a first power measure indicative of the sum of power spectral values in a third frequency band whose lower limit is greater than 70 Hz;
   calculating, based on the physiological signal data, a second power measure indicative of the sum of power spectral values in a fourth frequency band containing substantially EEG signal components only; and
   deriving the second parameter from the ratio of the first and second power measures.

14. A method according to claim 13, wherein the third frequency band extends from a frequency of about 105 Hz to a frequency of about 145 Hz.

15. A method according to claim 13, wherein the fourth frequency band extends from a frequency of about 11 Hz to a frequency of about 20 Hz.

16. A method according to claim 13, wherein the deriving step further includes calculating the logarithm of the ratio of the first and second power measures.

17. An apparatus for monitoring the cerebral state of a subject, the apparatus comprising:
   means for receiving physiological signal data from a subject, the physiological signal data including EEG signal components;
   first calculation means for deriving a first parameter from the physiological signal data, wherein the first parameter is indicative of the relative magnitudes of a first sum of k-th order spectral values and a second sum of n-th order spectral values, wherein the second sum is calculated over a first frequency band lying above high frequency EEG activity and consisting mostly of EMG activity, and wherein k is an integer greater than two and n is an integer greater than one; and
   second calculation means for forming a state index that has a predetermined relationship with the first parameter, the state index being indicative of the cerebral state of the subject.

18. The apparatus according to claim 17, further comprising:
   third calculation means for deriving a first parameter from the physiological signal data, wherein the first parameter is indicative of the sum of spectral values of the physiological signal data in a second frequency band lying above high frequency EEG activity and consisting mostly of EMG activity;
   fourth calculation means for forming the state index which is dependent on the first parameter and the second parameter.

19. An apparatus according to claim 18, further comprising fifth calculation means for deriving, based on the physiological signal data, a burst suppression index indicative of burst suppression in the physiological signal data.

20. An apparatus according to claim 19, wherein the fourth calculation means are configured to form a weighted sum of the first parameter, the second parameter, and the burst suppression index.

21. An apparatus according to claim 18, wherein the third calculation means are configured to derive the second parameter based on power spectral values of the physiological signal in the second frequency band.

22. An apparatus according to claim 18, wherein the first calculation means are configured to derive the first and second sums of the first parameter based on bispectral values.

23. An apparatus according to claim 21, wherein the third calculation means are configured to calculate, based on the physiological signal data, a first power measure indicative of the power of the physiological signal data in a third frequency band whose lower limit is greater than 70 Hz, a second power measure indicative of the power of the physiological signal data in a fourth frequency band containing substantially LEG signal components only, arid to derive the second parameter from the ratio of the first and second power measures.

24. An apparatus according to claim 23, wherein the third frequency band extends from a frequency of about 105 Hz to a frequency of about 145 Hz.

25. An apparatus according to claim 23, wherein the fourth frequency band extends from a frequency of about 11 Hz to a frequency of about 20 Hz.

26. An apparatus according to claim 17, wherein the first calculation means are configured to derive the first parameter, wherein the first calculation means are configured to calculate the ratio of the first and second sums.

27. An apparatus according to claim 26, wherein the first frequency band extends from a frequency of about 80 Hz to a frequency of about 95 Hz.

28. An apparatus according to claim 27, wherein the first calculation means are configured to calculate the first sum over a frequency band extending from a frequency of about 0.5 Hz to a frequency of about 95 Hz.

29. An apparatus according to claim 23, wherein the first calculation means are configured to calculate a logarithm of the ratio of the first and second power measures.

30. An apparatus according to claim 26, wherein the first calculation means are further configured to calculate a logarithm of the ratio of the first and second sums.

31. An apparatus for monitoring the cerebral state of a subject, the apparatus comprising:
   a first data processing unit configured to receive physiological signal data from a subject, the physiological signal data including EEG signal components;
   a second data processing unit configured to derive a first parameter and a second parameter from the physiological signal data, wherein the first parameter is indicative of the sum of spectral values of the physiological signal data in a first frequency band lying above high frequency EEG activity and consisting mostly of EMG activity and the second parameter is indicative of the relative magnitudes of a first sum of k-th order spectral values and a second sum of n-th order spectral values, wherein the second sum is calculated over a second frequency band lying above high frequency EEG activity and consisting mostly of EMG activity, and wherein k is an integer greater than two and n is an integer greater than one; and
   a third data processing unit configured to form a state index which is dependent on the first parameter and the second parameter, the state index being indicative of the cerebral state of the subject.

32. A computer program product for an apparatus monitoring a patient, the computer product comprising:
   a first program code portion which, when executed by the apparatus, is for receiving physiological signal data obtained from a subject, the physiological signal data including EEG signal components; and
   a second program code portion which, when executed by the apparatus, is configured to derive a first parameter and a second parameter from the physiological signal data, wherein the first parameter is indicative of the sum of spectral values of the physiological signal data in a first frequency band lying above high frequency EEG activity and consisting mostly of EMG activity and the second parameter is indicative of the relative magnitudes of a first sum of k-th order spectral values and a second sum of n-th order spectral values, wherein the second sum is calculated over a second frequency band lying above high frequency EEG activity and consisting mostly of EMG activity, and wherein k is an integer greater than two and n is an integer greater than one.

33. A computer program product according to claim 32, wherein the second program code portion, when executed by the apparatus, is further configured to supply the at least one parameter to the apparatus.

34. A computer program product according to claim 32, further comprising a third program code portion configured to form a state index which is dependent on the at least one parameter, the state index being indicative of the cerebral state of the subject.

* * * * *